United States Patent [19]
Förster

[11] Patent Number: 5,320,525
[45] Date of Patent: Jun. 14, 1994

[54] ORTHODONTIC BRACKET

[75] Inventor: Rolf Förster, Pforzheim, Fed. Rep. of Germany

[73] Assignee: Bernard Förster GmbH, Pforzheim, Fed. Rep. of Germany

[21] Appl. No.: 893,437

[22] Filed: Jun. 4, 1992

[30] Foreign Application Priority Data

Jun. 4, 1991 [DE] Fed. Rep. of Germany ....... 4118248

[51] Int. Cl.⁵ ................................................ A61C 3/00
[52] U.S. Cl. ............................................ 433/9; 433/8
[58] Field of Search ........................... 433/8, 9, 16, 17

[56] References Cited

U.S. PATENT DOCUMENTS 3,964,165 6/1976 Stahl ..................................... 433/8
4,799,882 1/1989 Kesling ................................. 433/8

Primary Examiner—John J. Wilson
Attorney, Agent, or Firm—Dvorak and Traub

[57] ABSTRACT

This invention relates to an orthodontic bracket for retaining a wire arch for tooth correction, which bracket comprises a base part having single or double wings and are formed with an open-ended and open-topped transverse groove for receiving the wire arch, and also comprises a footpad secured to the base part and adapted to be adhesively joined to an adjacent tooth surface. A groove is formed in the base part and/or in the pad and extends on the underside thereof or particularly a tunnel is formed in said base part and/or pad, which groove or tunnel extends in the direction in which the wings are spaced apart and serves to anchor partial wire arches.

2 Claims, 3 Drawing Sheets

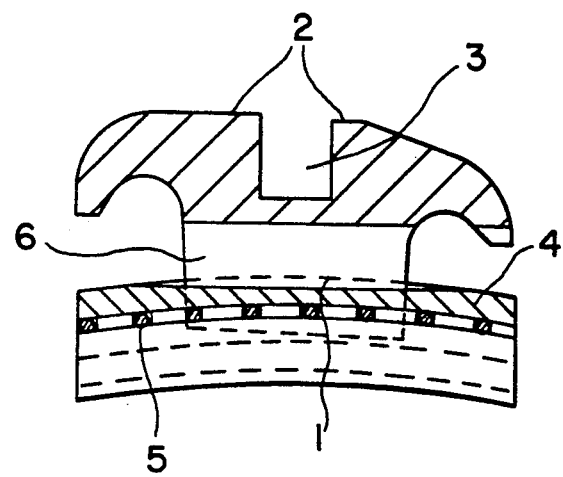
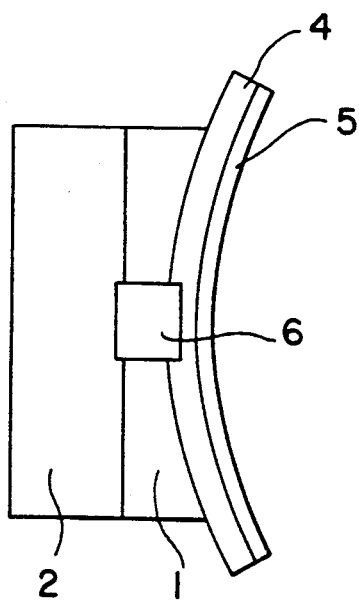
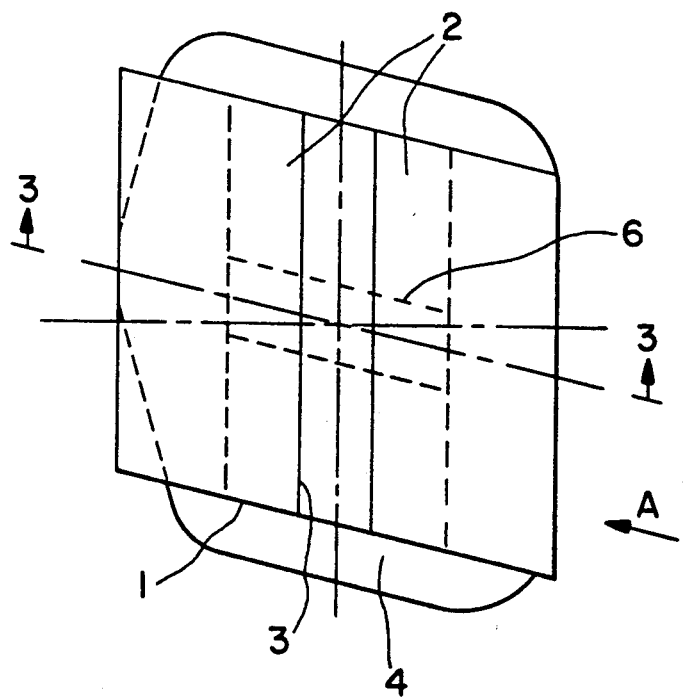

ORTHODONTIC BRACKET

BACKGROUND OF THE INVENTION

1. Field of the Invention

This invention relates to an orthodontic bracket for retaining a wire arch for tooth correction, which bracket comprises a base part having single or double wings and are formed with an open-ended and open-topped transverse groove for receiving the wire arch, and also comprises a footpad secured to the base part and adapted to be adhesively joined to an adjacent tooth surface.

2. Description of the Prior Art

Such brackets are used for the so-called full-arch technique, by which the following movements for correcting the tooth positions can be effected in dependence on the angular orientation of the transverse groove and the wing or wings and of the base surface of the pad relative to the orientation of the entire bracket:

a) A turning moment for a lingual-labial and buccal tilting of the teeth;
b) an angulation for a mesial-distal tilting of the teeth;
c) An inward and outward labial-lingual or buccal-lingual movement of the teeth; and
d) a rotation of the teeth.

Each bracket is designed to effect said movements to predetermined extents, which are selected by the orthodontic dentist in the so-called straight-arch technique.

In orthodontic treatment it is often also necessary to effect an individual or additional treatment of individual teeth or sets of teeth. It has previously been necessary to keep special brackets or buccal tubes for the so-called partial-arch technique in storage for that purpose.

In said partial-arch technique, an additional partial wire arch must be used, mainly adjacent to a canine, and said partial wire arch must extend as far as to the 6th and 7th molars. That requirement has previously been met in that an additional square-section tube was applied to the labial side of the canine. That practice involves the following inconveniences for the patient:

The square-section tube annoys the patient;
it promotes the accumulation of plaque;
it is not functionally satisfactory because it is spaced a large distance from the root of the tooth.

Said additional tubes are either separately attached to the tooth front or are secured to the bracket for the full-arch technique so that the volume and particularly also the overall height of the bracket are increased. This results in the above-mentioned disadvantages and renders the simultaneous use of such brackets for the full-arch technique and the partial-arch technique more difficult. Besides a large number of different brackets must be kept in stock by the dentist for the various uses.

SUMMARY OF THE INVENTION

It is an object of the invention to provide a bracket which can be used both in the full-arch technique and in the partial-arch technique at the same time without a need for structural alterations and in such a manner that the movements stated hereinbefore sub a) to d) can be effected to the specified extents.

In an orthodontic bracket of the kind defined first hereinbefore that object is accomplished in accordance with the invention in that a groove is formed in the base part and/or in the pad and extends on the underside thereof or particularly a tunnel is formed in said base part and/or pad, which groove or tunnel extends in the direction in which the wings are spaced apart and serves to anchor partial wire arches. As a result, brackets having a low overall height and a relatively small volume can be used individually or in combination for the full-arch technique and for the partial-arch technique in such a manner that the inconvenience for the patient and the storage requirements are decreased. Brackets having pairs of spaced apart wings may comprise at the top between the parallel slots between the wings of each pair a connecting portion, and the open-topped transverse groove may cross over or intersect said connecting portion whereas the groove formed on the underside of the base part and foot pad or the tunnel formed in the base part and footpad may extend in the direction in which the pairs of wings are spaced apart and may be used to anchor a partial wire arch.

BRIEF DESCRIPTION OF THE DRAWING

FIGS. 1 to 3 are a top plan view, side elevation and transverse sectional view, respectively, which show a bracket comprising two single wings.

DETAILED DESCRIPTION OF THE PREFERRED EMBODIMENTS

Figure 6:
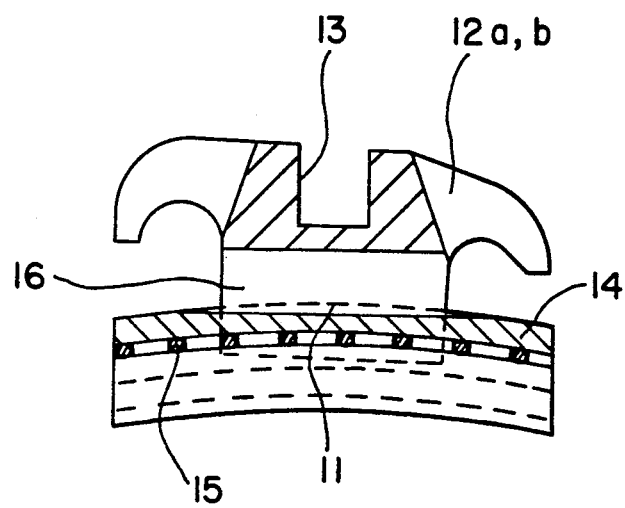
FIGS. 4 to 6 are a top plan view, side elevation, and transverse sectional view showing a bracket having two pairs of wings.

Further details of the orthodontic bracket in accordance with the invention will now be described with reference to three preferred embodiments shown in the drawing.

In the first embodiment shown in FIGS. 1 to 3 the bracket comprises a base part 1, which has two longitudinally spaced apart single wings 2 and is formed between said wings with an open-ended and open-topped transverse groove 3 for receiving the wire arch, not shown, that is used for the tooth correction in the full-arch technique. A foot pad 4 is secured to the base part and comprises a mesh 5, which is to be adhesively joined in known manner to the adjacent surface of a tooth to be corrected. In accordance with the invention the base part 1 and the footpad 4 are formed with a tunnel 6, which extends in the direction in which the wings 2 are spaced apart and serves to anchor a partial wire arch, not shown.

Figure 5:
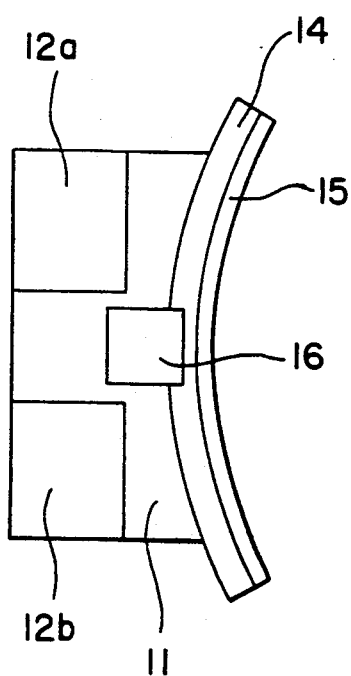
Figure 4:
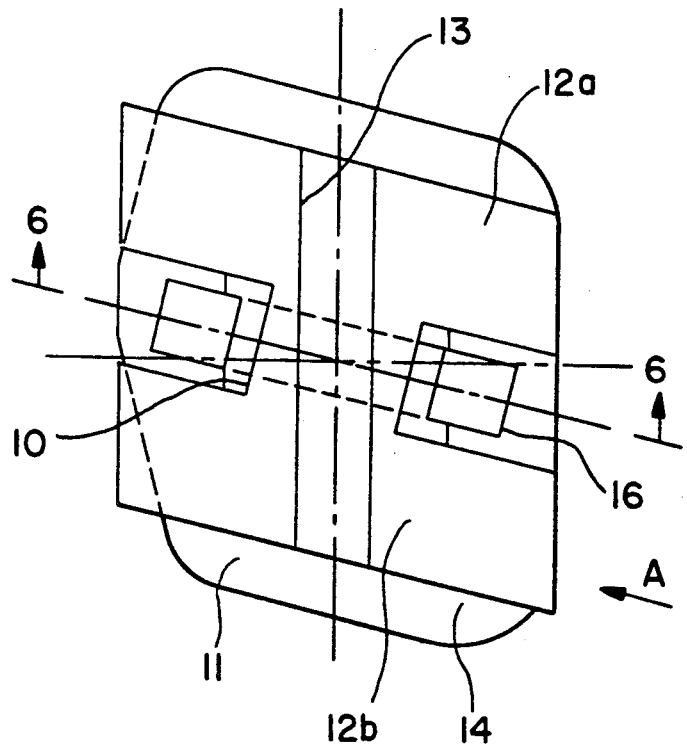

The second embodiment shown in FIGS. 4 to 6 comprises a base part 11 having four wings, namely two longitudinally spaced apart pairs of wings 12a and 12b, and formed between the wings of each pair with a slot 9 and comprising between the pairs of wings 12 and the parallel slots 9 a connecting portion 10. In a low bracket the open-ended groove 13 for receiving the wire arch, not shown, for the full-arch technique may intersect or cross the parallel slots 9. A footpad 14 is secured to the base part 11 and comprises a mesh 15 that is to be adhesively joined to an adjacent tooth surface, as in the first embodiment. In accordance with the invention the base part 11 and the footpad 14 are formed with a tunnel 16, which extends between the slots 9 in the direction in which the pairs of wings 12 are spaced apart and serves to anchor a partial wire arch, not shown.

Figure 9:
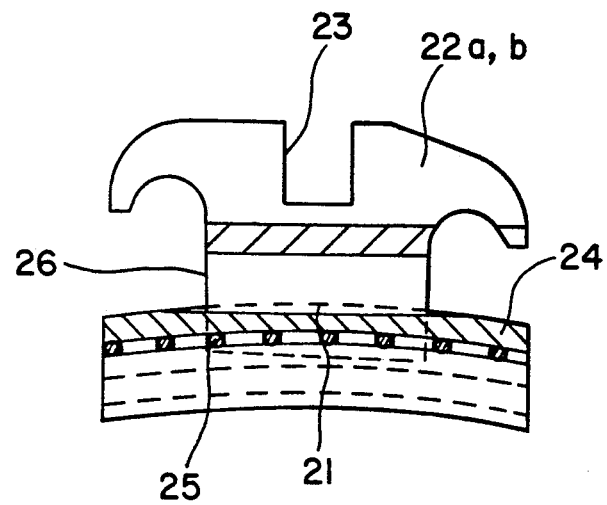
FIGS. 7 to 9 are a top plan view, side elevation, and transverse sectional view, respectively, which show another bracket comprising two pairs of wings.
Figure 8:
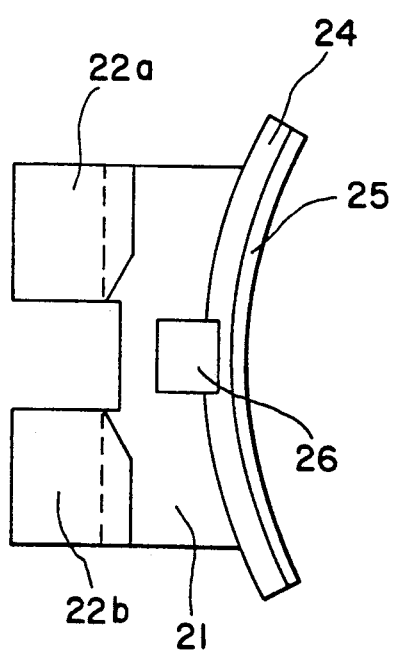
Figure 7:
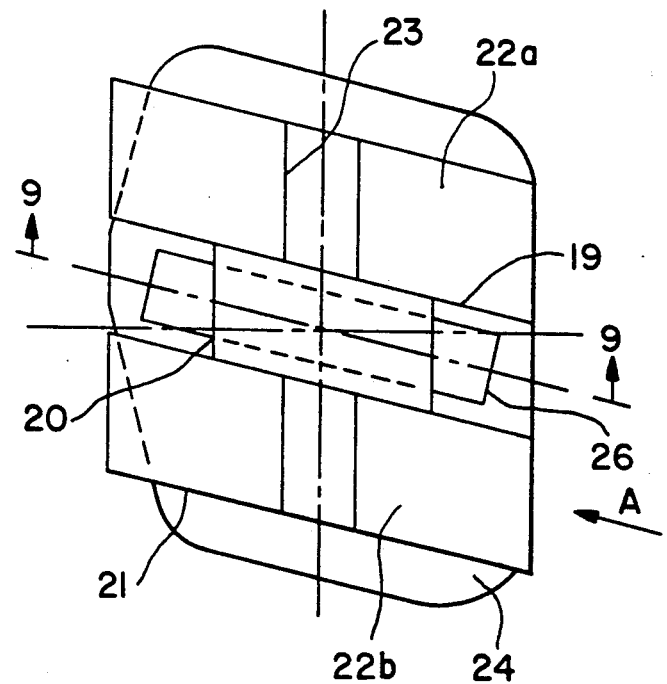

In the third embodiment shown in FIGS. 7 to 9 a base part 21 comprises four wings, namely, two longitudinally spaced apart pairs of wings 22a and 22b, and is formed between the wing of each pair with a slot 19 and comprises a connecting portion 20 between the pairs of wings 12 and the slots 19. In a relatively high bracket the open-ended transverse groove 23 for receiving the wire arch, not shown, for the full-arch technique, extends over and crosses the parallel slots 19. A footpad 24 is secured the base part 21 and comprises a mesh 25, which is to be adhesively joined to an adjacent tooth surface, as in the first and second embodiments. In accordance with the invention the base part 21 and the footpad 24 are formed with a tunnel 26, which extends in the direction in which the pairs of wings 22 are spaced apart and serves to anchor a partial wire arch, not shown.

In all cases the tunnel 6, 16 or 26 is composed of a groove in the base part 1, 11 or 21 and of a groove in the top portion of the footpad 4, 14, 24. These grooves are formed in the base part and footpad before the latter are joined. To allow for dimensional deviations, the groove in the footpad is somewhat wider than the groove in the base part. The tunnel in the bracket may be replaced by an open-bottomed groove, which is not shown herein. That groove or tunnel is used to receive a partial wire arch so that the bracket can be used for two orthodontic functions, namely, in a full-arch technique and in a partial-arch technique, at the same time.

The bracket in accordance with the invention will mainly be made of metal.

I claim:

1. In an orthodontic bracket for retaining a wire arch for tooth correction comprising a base part provided with longitudinally spaced apart parallel wings, and between said wings with an open-ended and open-topped transverse groove for receiving a wire arch, and a footpad secured to said base part and adapted to be adhesively joined to an adjacent tooth surface, the improvement residing in that an opening constituted by a tunnel formed in at least one of said base part and footpad, said opening for receiving a partial wire arch is formed in said bracket in addition to said transverse groove and extends in the direction in which said wings are spaced apart, wherein said tunnel is composed of an open-bottomed groove formed in said base part and of an open-topped groove formed in said footpad.

2. In an orthodontic bracket for retaining a wire arch for tooth correction comprising a base part provided with longitudinally spaced apart parallel wings, and between said wings with an open-ended and open-topped transverse groove for receiving a wire arch, and a footpad secured to said base part and adapted to be adhesively joined to an adjacent tooth surface, the improvement residing in that an opening constituted by a tunnel formed in at least one of said base part and footpad, said opening for receiving a partial wire arch is formed in said bracket in addition to said transverse groove and extends in the direction in which said wings are spaced apart, wherein said tunnel is composed of an open-bottomed groove formed in said base part and of an open-topped groove formed in said footpad, said groove in said footpad is wider than said open-bottomed groove in said base part.

* * * * *